United States Patent
Kosaka et al.

(10) Patent No.: US 10,234,456 B2
(45) Date of Patent: Mar. 19, 2019

(54) IMMUNOCHROMATOGRAPHY DEVICE FOR DETECTING RSV

(71) Applicants: Tanaka Kikinzoku Kogyo K.K., Tokyo (JP); ALFRESA PHARMA CORPORATION, Osaka-shi, Osaka (JP)

(72) Inventors: Mieko Kosaka, Ibaraki (JP); Hiromi Taguchi, Ibaraki (JP); Noboru Sakai, Ibaraki (JP); Daisuke Itoh, Hiratsuka (JP); Hisahiko Iwamoto, Hiratsuka (JP)

(73) Assignees: TANAKA KIKINZOKU KOGYO K.K., Tokyo (JP); ALFERESA PHARMA CORPORATION, Osaka (JP)

( * ) Notice: Subject to any disclaimer, the term of this patent is extended or adjusted under 35 U.S.C. 154(b) by 302 days.

(21) Appl. No.: 14/899,248

(22) PCT Filed: Jun. 20, 2014

(86) PCT No.: PCT/JP2014/066378
§ 371 (c)(1),
(2) Date: Dec. 17, 2015

(87) PCT Pub. No.: WO2014/203988
PCT Pub. Date: Dec. 24, 2014

(65) Prior Publication Data
US 2016/0139125 A1    May 19, 2016

(30) Foreign Application Priority Data
Jun. 21, 2013  (JP) ................. 2013-130095

(51) Int. Cl.
G01N 33/569    (2006.01)
B01D 15/26     (2006.01)
B01D 15/38     (2006.01)
C07K 16/10     (2006.01)

(52) U.S. Cl.
CPC ..... *G01N 33/56983* (2013.01); *B01D 15/265* (2013.01); *B01D 15/3819* (2013.01); *C07K 16/1027* (2013.01); *G01N 2333/135* (2013.01)

(58) Field of Classification Search
None
See application file for complete search history.

(56) References Cited

U.S. PATENT DOCUMENTS

| | | | |
|---|---|---|---|
| 2002/0001798 A1 | 1/2002 | Brams et al. | |
| 2002/0081573 A1* | 6/2002 | Lassen | G01N 33/56983 435/5 |
| 2008/0160508 A1 | 7/2008 | Imoarai et al. | |
| 2010/0015596 A1 | 1/2010 | Asaeda et al. | |
| 2011/0076268 A1* | 3/2011 | Williamson | C07K 16/1027 424/133.1 |

FOREIGN PATENT DOCUMENTS

| | | |
|---|---|---|
| CN | 101629959 A | 1/2010 |
| EP | 2145899 A1 | 1/2010 |
| JP | 2004-534513 A | 12/2005 |
| JP | 2008-014751 A | 1/2008 |
| JP | 2008-122372 A | 5/2008 |
| JP | 2008-164403 A | 7/2008 |
| JP | 2010-025745 A | 2/2010 |
| JP | 2012-083370 A | 4/2012 |
| WO | WO 2005015207 A2 | 2/2005 |

OTHER PUBLICATIONS

Kazushige Nagai et al., "Epidemics of variants in each of subgroup A and B of respiratory syncytial virus", Clinical Virology, Sep. 1991, vol. 19, No. 3, pp. 273 to 277.
K. Nagai et al. "Three antigenic variant groups in human respiratory syncytial virus subgroup B isolated in Japan", Arch Virol., 1993, vol. 128, No. 1/2, p. 55-63.
A. L. Clayton et al., "The selection and performance of monoclonal and polyclonal anti-respiratory syncytial virus (RS) antibodies in capture ELISAs for antigen detection", J. Virol Methods., Sep. 1987, vol. 17, No. 3/4, p. 247-261.
J. A. Beeler et al., Neutralization epitopes of the F glycoprotein of respiratory syncytial virus: effect of mutation upon fusion function. J.Virol. 1989, 63(7):2941.
International Preliminary Report on Patentability for PCT/JP2014/066378, dated Jun. 4, 2015.
CN, Office Action concerning application 201480035447.0, dated Oct. 27, 2016.
EP, European Extended Search Report concerning application 14814429.8, dated Dec. 20, 2016.
BD Diagnostics. Understanding RSV Testing, Technical Bulletin, vol. 1, No. 1, Sep. 2004, No. XP-002546681.
Kikuta, et al. Comparison of a Lateral-Flow Immunochromatogmphy Assay with Real-Time Reverse Transcription-PCR for Detection of Human Metapneumovirus. Journal of Clinical Microbiology, Mar. 2008; 46(3):928-932.

* cited by examiner

*Primary Examiner* — Benjamin P Blumel
(74) *Attorney, Agent, or Firm* — Orrick, Herrington & Sutcliffe LLP; Joseph A. Calvaruso (57) ABSTRACT

The present invention provides an easy-to-use and higher-sensitivity immunochromatography device for an RSV, the device using an antibody that binds specifically to F protein of the RSV in a determination region of a chromatography medium, a test kit by an immunochromatography method, and a method for detecting an RSV using these device and kit. The present invention relates to an immunochromatography device in which not only an antibody that binds specifically to F protein of an RSV but also an antibody that binds specifically to N protein of the RSV is solid-phased in a determination region of a chromatography medium. The present invention also relates to a test kit by an immunochromatography method, and a method for detecting an RSV using these device and kit.

10 Claims, 1 Drawing Sheet

IMMUNOCHROMATOGRAPHY DEVICE FOR DETECTING RSV

TECHNICAL FIELD

The present invention relates to an immunochromatography device in which at least two types of antibodies are immobilized, one of them is an antibody that specifically recognizes the F protein of respiratory syncytial virus (RSV) and the other one is an antibody that specifically recognizes the N protein of RSV. The present invention also relates to an RSV test kit including the device.

BACKGROUND ART

RSV is a virus that causes respiratory tract infections, and cells infected with the virus form multinucleated giant cells (syncytia). RSV can cause infection at any age during our lifetime, but it is the pathogen that causes very severe symptoms in especially infants. Fifty to seventy percent or more of infants get infected with this virus within a year after birth, and almost all the children acquire antibody by the age of 3. However, infection within several weeks to several months after birth causes most severe symptoms. In the case of low-birth-weight babies or children with impaired immunity or underlying cardiorespiratory disease, the risk of increased severity increases. There is a report that the fatality rate from RSV infection is 1 to 3%. However, the fatality rate widely varies depending on the situation. It has been reported during the 1980s that the fatality rate is as high as 37% according to research on hospitalized children with underlying heart disease.

RSV infections have been reported all over the world irrespective of geographic or climatic conditions. Characteristically, RSV infections cause severe symptoms in immature infants in all the areas, and repeatedly break out every year in especially urban areas.

It has been reported that RSV infections account for about 50% of cases of pneumonia and 50 to 90% of cases of bronchiolitis in infants. The peak of the number of children hospitalized with lower respiratory tract disease, such as pneumonia or bronchiolitis, coincides with the peak of outbreak of RSV infections rather than influenza. During epidemics of RSV infections, RSV reinfection in older children or adults universally occurs. However, in contrast to severe symptoms in infants, older children or adults show only mild cold-like symptoms and often get better.

It is known that RSV is relatively unstable in the environment, but transmission of RSV infection efficiently occurs within families. A school-age child showing mild symptoms often introduces the virus into the family. There is also a report that 44% of families with a school-age child and an infant have an experience of intrafamilial transmission of RSV infection during its epidemic season. Main routes of RSV infection are large respiratory droplets and contact through hands or objects contaminated with respiratory secretions. Particularly, RSV infection occurs via close contact. Therefore, in order to prevent RSV infection in an infant, it is very important to accurately understand the presence or absence of RSV infection in other family members irrespective of the severity of symptoms. When any of the family members is confirmed RSV infection, it is very important to avoid contact with the infant and prevent contamination from secretions.

From the viewpoint of prevention and treatment of RSV infections, especially RSV infection in infants, there has been demand for a simple and higher-sensitive kit for rapidly diagnosing RSV infection. It is preferred that RSV-infected infants are appropriately treated as soon as possible, which requires a high-sensitive test kit that can give a test result in a short time but does not give a false-negative result even when a test is performed in an initial phase of infection in which the amount of the virus is small. Further, when a member of a family with an infant shows cold-like symptoms and is suspected of RSV infection, a simple test method is required by which the presence or absence of RSV infection can be determined with less physical and financial burden.

As simple, high-sensitive, and rapid diagnostic kits that satisfy such a requirement, immunochromatographic RSV test kits have been developed. Currently, more than one immunochromatographic test kit is known which can detect a virus antigen and can be used to assist the diagnosis of RSV infections. However, all these kits use antibodies against F protein of RSV (Patent Literatures 1 to 3).

The F protein of RSV is one of the two kinds of main glycoproteins present on the surface of RSV. On the surface of the virus, G protein is also present in addition to the F protein. The F protein is highly conserved between and within the subtypes A and B of RSV in homology, whereas the homology of the G protein between the subtypes is only about 53%. Research conducted by Beeler and Coelingh (1989) demonstrates that antibodies against the F protein of RSV can bind to all 14 clinical isolates isolated in various regions in the United States of America and Australia from 1956 to 1985 and the F protein is very highly conserved among the virus strains (Patent Literature 4, Non-Patent Literature 1).

Antibodies against the F protein have been used in RSV detection kits with the expectation that various clinical isolates can be detected without exception due to highly-conserved epitopes. However, RSV detection using such conventional RSV test kits involves a major problem that 30 to 40% of samples determined as positive by another test method are determined as negative. The reason why immunochromatographic test kits are likely to give false-negative results have been considered that antibodies against the F protein used in those kits do not have sufficient binding affinities. If the binding affinities are not sufficient, clear positive signals cannot be detected when the amount of the virus contained in samples are small and consequently, the samples are judged as false negative. In order to develop a high-sensitive test kit in which a clear signal can be detected even when the amount of the virus is small, an attempt has been made to prepare a monoclonal antibody having a high affinity for the F protein of RSV (Patent Literature 5). However, it is very difficult to develop an RSV test kit which can detect clinical isolates without exception as well as can achieve a practical positive detection rate, simply by increasing the affinity of an antibody for the F protein.

CITATION LIST

Patent Literatures

Patent Literature 1: JP 2008-14751 A
Patent Literature 2: JP 2008-122372 A
Patent Literature 3: JP 2008-164403 A
Patent Literature 4: JP 2004-534513 A
Patent Literature 5: JP 2010-25745 A

Non Patent Literature

Non-Patent Literature 1: Journal of Virology, July 1989, Vol. 63, No. 7, p. 2941-2950

SUMMARY OF INVENTION

Technical Problem

The present invention provides a simple and high-sensitive immunochromatography device and an immunochromatographic test kit for RSV that include a chromatography medium having a determination region using an antibody that specifically binds to the F protein of RSV. The present invention also provides a method for detecting RSV using the device or the test kit, and a method for determining or diagnosing an RSV infection using the device or the test kit.

Further, the present invention provides; an immunochromatography device and an immunochromatographic test kit that are capable of efficiently detecting RSV even when the amount of the virus contained in a sample is small, a method for detecting RSV using the device or the test kit, and a method for determining or diagnosing an RSV infection using the device or the test kit.

Solution to Problem

In order to allow a determination region to efficiently capture RSV contained in a sample to improve the sensitivity of an immunochromatography device, the present inventors have studied a higher affinity antibody against the F protein immobilized on the determination region. Furthermore, the present inventors have studied the immobilization of the antibody against the F protein of RSV in combination with an antibody against another protein of RSV. As a result, the present inventors have surprisingly found that when the antibody against the F protein is immobilized in combination with an antibody against the N protein (nuclear protein) of RSV, signal of positive samples can be enhanced as compared to when the antibody against the F protein is singly immobilized. Further, the present inventors have found that when the antibody against the F protein is immobilized on the determination region in combination with the antibody against the N protein, a sample can be accurately determined as positive even when the sample is determined as negative by a conventional immunochromatographic method. Using the conventional immunochromatographic methods, some samples are not determined accurately as positive even though the samples have been confirmed the presence of a sufficient amount of the virus by PCR method or the like. The present inventors have found that the samples are accurately determined by the combination of an antibody against the F protein and an antibody against the N protein on the determination region and that therefore positive concordance rates of the immunochromatographic method with other test methods is able to be significantly improved.

That is, the present invention relates to an immunochromatography device including a chromatography medium as a component in which at least one antibody that specifically binds to the F protein and at least one antibody that specifically binds to the N protein are immobilized on a determination region.

Further, the present invention relates to an RSV test kit including the immunochromatography device.

Further, the present invention relates to a method for detecting RSV using an immunochromatography device in which at least one antibody that specifically binds to the F protein and at least one antibody that specifically binds to the N protein are immobilized on a determination region. Further, the present invention relates to a method for improving an RSV detection rate by an immunochromatographic method including a process of bringing a sample liquid into contact with at least one antibody against the F protein and at least one antibody against the N protein that are immobilized on a determination region.

Embodiments of the present invention will be described in more detail with reference to the following (1) to (12).

(1) An immunochromatography device including a chromatography medium having a determination region on which at least one antibody that specifically binds to an F protein of RSV and at least one antibody that specifically binds to an N protein of RSV are immobilized.

(2) The immunochromatography device according to the above (1), substantially including a sample addition part, the chromatography medium, and an absorption part.

(3) The immunochromatography device according to the above (2), further including a labeling reagent-holding part.

(4) The immunochromatography device according to the above (1) to (3), wherein the antibody that specifically binds to the F protein is at least one antibody that specifically binds to one or both of an F protein of subgroup A of RSV and an F protein of subgroup B of RSV.

(5) An immunochromatographic test kit for RSV including: an immunochromatography device including a chromatography medium having a determination region on which at least one antibody that specifically binds to an F protein of RSV and at least one antibody that specifically binds to an N protein of RSV are immobilized; and a sample diluent.

(6) The immunochromatographic test kit for RSV according to the above (5), wherein the immunochromatography device substantially includes a sample addition part, the chromatography medium, and an absorption part.

(7) The immunochromatographic test kit for RSV according to the above (6), wherein the immunochromatography device further includes a labeling reagent-holding part.

(8) The immunochromatographic test kit for RSV according to the above (6), further including a labeling reagent solution.

(9) A method for detecting RSV using an immunochromatography device having a determination region on which at least one antibody that specifically binds to an F protein of RSV and at least one antibody that specifically binds to an N protein of RSV are immobilized.

(10) An immunochromatographic method for detecting RSV, including:

(a) a process of supplying a sample liquid containing a sample to an immunochromatography device in which at least one antibody that specifically binds to an F protein of RSV and at least one antibody that specifically binds to an N protein of RSV are immobilized on a determination region;

(b) a process of allowing the sample liquid supplied in the process (a) to pass through the determination region together with a labeling reagent;

(c) a process of bringing the sample liquid containing the labeling reagent into contact with the immobilized antibodies in the determination region; and (d) a process of determining the sample as "RSV positive" when coloring caused by the labeling reagent is detected.

(11) The immunochromatographic method for detecting RSV according to the above (10), further including a process of diluting the sample with a sample diluent before the sample is supplied to the immunochromatography device.

(12) A method for improving an RSV detection rate by the method according to the above (10) or (11).

Advantageous Effects of Invention

The immunochromatography device according to the present invention includes a chromatography medium having a determination region formed by immobilizing at least one antibody that specifically binds to the F protein of RSV and at least one antibody that specifically binds to the N protein of RSV thereon. The use of a mixture of these two kinds of antibodies in the same determination region makes it possible to efficiently capture an RSV antigen and to enhance a signal obtained by measuring a positive sample as compared to a test kit in which one of the antibodies is singly immobilized. Therefore, the immunochromatography device according to the present invention provide a high-sensitive, high-reliable and simple RSV rapid diagnostic kit. Since an enhanced positive signal is obtained, RSV can be detected with high sensitivity even when the amount of the virus contained in a sample is small. Therefore, the presence of RSV can be accurately determined even when a sample is collected from a patient in the initial phase of infection. Further, even when a sample is diluted as needed, RSV can be detected with high sensitivity. Therefore, it is possible to prevent a problem caused by directly developing a viscous sample such as nasal swab or pharyngeal swab. The viscous sample has a problem that the sample cannot move in the chromatography medium so that determination is impossible or has a problem that a component, other than RSV, contained in the sample is adsorbed to the chromatography medium so that a non-specific signal is generated. The immunochromatography device according to the present invention can prevent these problems.

Further, the antibody that specifically binds to the N protein immobilized on the determination region in the present invention allows the determination region to capture an RSV antigen even when the antigenicity of the F protein contained in a sample is lost. Therefore, according to the present invention, it is possible to accurately determine an RSV-containing sample as positive. Since the presence of RSV can be reliably determined even when the antigenicity of the F protein is lost, it is also possible to pretreat or store a sample under more stringent conditions that influence the antigenicity of the F protein. Therefore, a sample, which is conventionally unsuitable for immunochromatography for the reason of, for example, too high viscosity, can be denatured by appropriately setting the conditions of pretreatment or storage so that the sample can move in the chromatography medium within a predetermined time. This makes it possible to achieve a rapid and accurate test irrespective of the state of a sample.

The immunochromatography device according to the present invention uses the antibody against the F protein in combination with the antibody against the N protein, and therefore it is possible not only to detect low-concentration RSV with high sensitivity but also to accurately determine a sample containing a sufficient amount of the virus as positive without exception. As a result, a virus detection rate can be significantly increased as compared to conventional immunochromatographic test kits, and positive concordance rates with other test methods can also be significantly improved. Therefore, the present invention made it possible to provide a useful RSV test method that achieves not only simplicity and rapidness that are advantages particular to immunochromatography but also a virus detection rate comparable to those of other test methods.

BRIEF DESCRIPTION OF DRAWINGS

FIG. 1 is a schematic sectional view of an immunochromatography device. The device usually includes a sample addition part (1), a chromatography medium (3) having a determination region (4), an absorption part (5), and a backing sheet (6), and may optionally include a labeling reagent-holding part (2).

DESCRIPTION OF EMBODIMENTS

Embodiments of the present invention will be described in more detail.

In the present invention, both an antibody that specifically binds to the F protein of RSV and an antibody that specifically binds to the N protein of RSV are used in a determination region. And the presence of RSV in a sample can be determined by detecting the F protein and/or N protein of RSV in the sample based on immunochromatographic principles.

In the present invention, the "antibody that specifically binds to the F protein" of RSV refers to an antibody that specifically recognizes and binds to the F protein of infective RSV for humans.

RSV is a type of RNA virus belonging to the family Paramyxoviridae, and is classified into two subtypes A and B. The genetic sequence of RSV has already been determined.

The F protein of RSV is one of three glycoproteins present on the surface of RSV. The F protein is also called fusion protein because the F protein promotes fusion between the envelope membrane of the virus and the cell membrane of a sensitive cell to allow the ribonucleoprotein of the virus to enter the cytoplasm of the cell. The F protein further promotes fusion between the cell membrane of a virus-infected cell and the cell membrane of a cell adjacent to the virus-infected cell so that a syncytium is formed.

The F protein is a heterodimeric protein of about 70 kDa in which an F1 polypeptide of about 50 kDa and an F2 polypeptide of about 20 kDa are linked by disulfide binding. The F1 polypeptide and the F2 polypeptide are generated by cleaving an F protein precursor called F0.

The F protein amino acid sequences of some RSV strains are known. For example, the amino acid sequence of RSV Long strain is disclosed under accession number P12568 in NCBI GenBank database.

In the present invention, the antibody that specifically binds to the F protein of RSV is not particularly limited as long as the antibody specifically binds to the F protein of an RSV strain infective for humans. The antibody may recognize any epitope, for example, an epitope on the F1 polypeptide, an epitope on the F2 polypeptide, or a three-dimensional epitope formed by disulfide binding between them. However, in order to prevent the failure of virus detection due to the difference in subtype, an antibody is preferred which recognizes an epitope common to the subtypes A and B of RSV and binds to the F protein from each virus strain of subtype A and subtype B.

In the present invention, the "antibody that specifically binds to the N protein" of RSV refers to an antibody that specifically recognizes and binds to the N protein of infective RSV for humans.

The N protein of RSV is also called nuclear protein, and is composed of 391 amino acid residues. The N protein is a component of a ribonucleoprotein complex called nucleocapsid, and surrounds the genomic RNA of RSV to form a helical structure. The N protein amino acid sequences of some RSV strains are known. For example, the amino acid sequence of RSV Long strain is disclosed under accession number DD857370 in NCBI GenBank database. The amino acid sequence of the N protein is highly conserved among RSV strains of subtypes A and B.

In the present invention, the antibody that specifically binds to the N protein of RSV is not particularly limited as long as the antibody specifically binds to the N protein of an RSV strain infective for humans. The antibody may recognize any epitope on the N protein. However, in order to prevent the failure of virus detection due to the difference in subtype, an antibody is preferred which recognizes an epitope common to the subtypes A and B of RSV and binds to the N protein from each virus strain of subtype A and subtype B.

The antibody used in the present invention may be a monoclonal or polyclonal antibody or an antigen-binding fragment thereof. However, the antibody is preferably monoclonal in consideration of high binding affinity, supply stability, ease of product quality control, etc.

The antibody usable in the present invention is producible according to known methods or is commercially available.

The antibody that recognizes the F protein or N protein used in the present invention is producible by administering the F protein or N protein of RSV used as an immunogen to an antibody-producing animal such as a mouse, rat, guinea pig, dog, goat, sheep, pig, horse, or cow. The F protein or N protein of RSV used as an immunogen may be in any form as long as the F protein or N protein of RSV can exert its action as an immunogen. For example, the F protein or N protein administered may be in the form of purified RSV, RSV-infected cells or an extract thereof, the purified protein, or a synthetic peptide from a part of the amino acid sequence of the protein. As described above, the amino acid sequences of the F protein and of the N protein for preparation of synthesize peptides are known.

When the antibody used in the present invention is polyclonal, the polyclonal antibody can be prepared in the usual manner. For example, the immunogen is administered to an antibody-producing animal, and then blood is collected from the animal. The blood is purified, for example, by affinity chromatography using a carrier with the F protein or N protein to obtain immunoglobulin fraction that causes an antigen-antibody reaction with the F protein or N protein of RSV but causes substantively no antigen-antibody reaction with other components of RSV.

When the antibody used in the present invention is monoclonal, the monoclonal antibody is producible by, for example, preparing hybridomas that produce a desired antibody in the usual manner. Antibody-producing hybridomas may be prepared by, for example, administering the immunogen to an animal, harvesting spleen cells from the animal, and then fusing the spleen cells with tumor cells such as myeloma cells in known technique (see, for example, Nature, 256: 495-497 (1975)).

From the hybridomas obtained by cell fusion, those that produce a desired antibody may be selected by a screening method such as solid-phase ELISA using a microplate having the F protein or the N protein immobilized thereon.

The antibody used in the present invention may be prepared by culturing the hybridomas in a culture medium usually used for cell culture and collecting the antibody from the culture supernatant. Alternatively, the antibody used in the present invention may be prepared by injecting the hybridomas into the peritoneal cavity of an animal, that is the same species of animals from which the hybridomas are derived, to accumulate ascites and collecting the antibody from the ascites.

The antibody that recognizes the F protein or N protein used in the present invention may be producible in the above manner, but may be also commercially available from more than one manufacturer as described in, for example, JP 2004-511807A. In the present invention, such a commercially-available antibody may be used.

Figure 1:
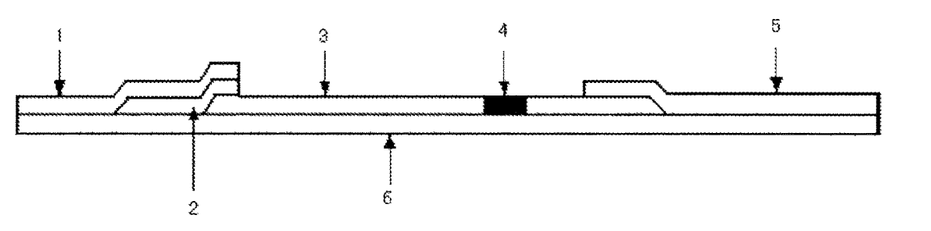

An "immunochromatography device" according to the present invention substantially includes a sample addition part, a chromatography medium, and an absorption part, and may optionally include a labeling reagent-holding part.

The "chromatography medium" used in the present invention is not particularly limited as long as the chromatography medium is composed of a porous membrane so that a sample liquid containing a sample can move therein by capillary action, but a porous membrane having an average pore diameter of 0.3 to 15 µm is preferably used. The chromatography medium is preferably made of an inactive material that does not react with components dissolved in a sample and that can immobilize an antibody thereon. Examples of such an inactive material include nitrocellulose, cellulose acetate, nylon, polyethersulfone, polyvinyl alcohol, polyesters, glass fibers, polyolefins, cellulose, and synthetic polymers made of blend fibers thereof.

In the present invention, the antibody that specifically binds to the F protein of RSV and the antibody that specifically binds to the N protein of RSV are immobilized on part of the chromatography medium to form a "determination region".

The antibody against the F protein and the antibody against the N protein may be jointly immobilized on the entire region of the determination region, or may be immobilized separately on their respective divided regions of the determination region. However, the two antibodies are preferably immobilized jointly on the same region of the determination region for the reason that the effect of enhancing a positive signal can be obtained.

In the present invention, the ratio between the antibody against the F protein of RSV and the antibody against the N protein of RSV is not particularly limited as long as both the antibodies are present in the determination region. Preferably, the proportion of the antibody specific to the N protein is larger than the proportion of the antibody specific to the F protein. The ratio of the anti-F protein antibody to the anti-N protein antibody present in the determination region (anti-F protein antibody/anti-N protein antibody) is preferably 1/1 to 1/5, more preferably 1/3 to 1/4.

The immobilization of the antibody on the chromatography medium may be performed by physical adsorption or chemical binding. In the case of physical adsorption, the antibody can be immobilized by applying a solution obtained by diluting the antibody with a buffer solution or the like onto the chromatography medium and drying the solution. The immobilization of the antibody against the F protein and the antibody against the N protein can be performed by applying one of these antibodies onto the chromatography medium, drying the applied antibody, and then applying the other antibody onto a different region or the same region. Alternatively, the immobilization of the antibody against the F protein and the antibody against the N protein may be performed by previously mixing the antibody against the F protein and the antibody against the N protein in a desired ratio, applying the mixture in a desired position on the chromatography medium, and drying the mixture.

After the determination region is formed by immobilizing the antibodies on the chromatography medium, if necessary, the chromatography medium may be subjected to blocking treatment to prevent a non-specific reaction. The blocking treatment can be performed using a protein such as bovine serum albumin, skimmed milk, casein, or gelatin or a commercially-available blocking agent such as Blocking Peptide Fragment (manufactured by TOYOBO) or a hydrophilic macromolecular polymer.

The "sample addition part" of the immunochromatography device according to the present invention is a site to which a sample liquid containing a sample is supplied and which is provided so as to be connected to the chromatography medium through capillary tubes. The material of the sample addition part is not particularly limited as long as a sample liquid can move by capillary action, but is generally selected from porous materials such as rayon, cupra, filter paper, and glass-fiber filter paper so that the purpose of the sample addition part is achieved.

The "absorption part" of the immunochromatography device according to the present invention is a site where a sample and a labeling reagent are absorbed. A sample liquid supplied to the sample addition part passes through the determination region of the chromatography medium and is absorbed by the absorption part. The material of the absorption part is not particularly limited as long as excess sample and labeling reagent can be quickly absorbed, and is selected from porous materials such as cellulose, filter paper, and glass-fiber filter paper so that the purpose of the absorption part is achieved. The absorption part is provided so as to be connected to the chromatography medium through capillary tubes.

The chromatography device according to the present invention substantially includes the chromatography medium, the sample addition part, and the absorption part, but may further include a backing sheet to improve handleability. The backing sheet supports the chromatography medium, which makes it easy to handle the chromatography medium to which the sample addition part and the absorption part are attached. The material of the backing sheet is not particularly limited as long as the backing sheet can achieve its purpose, but a colorless or white plastic is generally preferably used.

In the chromatography device according to the present invention, an F protein antigen and/or an N protein antigen contained in a sample are/is captured in the determination region by the anti-F protein antibody and the anti-N protein antibody immobilized on the determination region. These antigens captured in the determination region further bind to a labeling reagent so that their presence is visualized.

The "labeling reagent" used in the present invention includes an antibody that specifically binds to the F protein and/or an antibody that specifically binds to the N protein and a labeling substance. The labeling reagent used in the present invention allows an F protein antigen and an N protein antigen that are contained in a sample to indirectly bind to the labeling substance through the antibody.

The antibody that can be used for the labeling reagent used in the present invention is not particularly limited as long as the antibody can bind to an F protein antigen or an N protein antigen captured by the anti-F protein antibody and the anti-N protein antibody immobilized on the determination region. For example, an RSV-specific polyclonal antibody or an F protein- or N protein-specific polyclonal or monoclonal antibody can be used, but an F protein-specific monoclonal antibody and an N protein-specific monoclonal antibody are preferably used. More preferably, an F protein-specific monoclonal antibody and an N protein-specific monoclonal antibody are used which respectively recognizes an epitope different from the epitope recognized by the respective monoclonal antibody immobilized on the determination region. The labeling substance that can be used for the labeling reagent used in the present invention is not particularly limited as long as the labeling substance can generate a visible signal in a state where the labeling substance indirectly binds to the determination region through the antigen and the antibody. However, an enzyme or an insoluble carrier is generally preferably used. Examples of the enzyme that can be used as the labeling substance include alkaline phosphatase, horseradish peroxidase, β-galactosidase, urease, and glucose oxidase. The enzyme is used in combination with a substrate that is converted into a colored product. The insoluble carrier that can be used as the labeling substance is not particularly limited as long as the insoluble carrier is colored and has a particle diameter that allows it to move in the porous chromatography medium by capillary action. Examples of the insoluble carrier include colloidal metal particles, colloidal metal oxide particles, colloidal non-metal particles, and latex particles. Preferably, colloidal metal particles having an average particle diameter of 1 nm to 500 nm are used, and more preferably colloidal gold particles having an average particle diameter of 40 nm to 100 nm are used.

The labeling reagent used in the present invention can be produced by attaching the antibody that specifically binds to the F protein or N protein to the labeling substance by a known method such as physical adsorption or chemical binding. For example, a labeling reagent including an antibody and colloidal gold particles can be prepared in the following manner. An antibody is added to a solution in which gold particles are colloidally suspended to physically adsorb the antibody to the gold particles, and then a bovine serum albumin solution, the above-described blocking agent, or the like is added thereto to block the surface of the particles to which the antibody has not been attached.

When a monoclonal antibody against the F protein and a monoclonal antibody against the N protein are used as the antibody, these antibodies may be previously mixed in a desired ratio and then may be attached to colloidal gold particles. The labeling reagent produced in this manner can bind to both the F protein and the N protein captured in the determination region. Alternatively, two or more kinds of gold particles different in antibody attached thereto may be mixed in a desired ratio, which also makes it possible to produce a labeling reagent that can bind to the F protein and the N protein. The latter production method is preferred because the ratio between the anti-F protein antibody and the anti-N protein antibody contained in the labeling reagent can be strictly controlled. The ratio between the anti-F protein antibody and the anti-N protein antibody contained in the labeling reagent is not particularly limited, but is preferably the same as the ratio between these antibodies present in the determination region.

In one embodiment of the present invention, the labeling reagent is held in a dry state in the labeling reagent-holding part optionally provided in the immunochromatography device. In the present invention, the labeling reagent-holding part may be provided between the sample addition part and the determination region in the immunochromatography device. The labeling reagent held in the labeling reagent-holding part is dissolved in a sample liquid supplied to the chromatography device and passes through the determination region together with an RSV antigen contained in a sample.

In the present invention, the material of the labeling reagent-holding part is not particularly limited as long as the labeling reagent can be held in a dry state and the labeling reagent-holding part can be provided so as to be connected to the chromatography medium through capillary tubes. Examples of such a material include cellulose filter paper, glass fiber filter paper, and nylon non-woven fabric. The labeling reagent-holding part may contain a sugar such as saccharose, sucrose, trehalose, maltose, or lactose or a sugar alcohol such as mannitol to improve the resolubility of the labeling reagent.

In another embodiment of the present invention, the labeling reagent is included in a test kit in the form of solution as a component other than the immunochromatography device. The labeling reagent solution can be supplied to the chromatography device in any manner as long as the labeling reagent can pass through the determination region together with an RSV antigen in a sample. The labeling reagent solution can also be supplied in any manner as long as the labeling reagent can bind to the RSV antigen without interfering with the capture of the RSV antigen by the antibody immobilized on the determination region. For example, the labeling reagent solution may be mixed with a sample liquid and then be supplied to the sample addition part of the immunochromatography device, or the labeling reagent solution may be supplied to the sample addition part subsequently to the supply of a sample liquid.

The "sample" which apply to the present invention to determine whether RSV is present therein is not particularly limited as long as the sample is a liquid biological sample suspected to contain RSV. Preferred examples of such a sample include nasal swab, pharyngeal swab, nasal aspirate, nasal discharge, and nasal wash.

When a determination as to whether RSV is present in a nasal swab sample, pharyngeal swab sample, nasal aspirate sample, nasal discharge sample, or nasal wash sample is made according to the present invention, such a liquid sample may be directly supplied to the immunochromatography device and developed. However, such a highly viscous sample may be diluted with a sample diluent before it is supplied in order to facilitate its movement in the chromatography medium. In the present invention, the "sample liquid" means a liquid sample itself or a sample diluted with a sample diluent.

The "sample diluent" used in the present invention can be prepared by adding a salt and a buffering agent for adjusting pH to water used as a solvent. Further, a surfactant and a vinyl-based water-soluble polymer may be added to the sample diluent for the purpose of improving the flowability of a sample and reducing a non-specific reaction resulting from a component other than RSV contained in a sample.

The salt used for the sample diluent used in the present invention is not particularly limited as long as the salt is obtained by a reaction between an acid and a base. Examples of such a salt include alkali metal inorganic salts such as sodium chloride and potassium chloride. Preferably, sodium chloride is used.

The buffering agent used for the sample diluent used in the present invention is not particularly limited as long as the pH of the solution can be kept constant even when a sample is added, but is preferably one that can keep the pH in the range of 7 to 11. For example, a phosphate, a citrate, a borate, a Tris buffering agent, or a Good's buffering agent is used.

The surfactant used for the diluent used in the present invention is preferably a non-ionic surfactant, more preferably a non-ionic surfactant having a hydrophilic-lipophilic balance (HLB value) of 13 to 18, even more preferably a polyoxyethylene-based surfactant having an HLB value of 13 to 18. Preferred examples of the surfactant include polyoxyethylene alkyl ethers, polyoxyethylene sorbitan fatty acid esters (trade name "Tween" series), polyoxyethylene p-t-octylphenyl ethers (trade name "Triton" series), and polyoxyethylene p-t-nonylphenyl ethers (trade name "Triton N" series). These surfactants may be used singly or in combination of two or more of them. The non-ionic surfactant content of the sample diluent is not particularly limited, but is in the range of 0.01 to 10.0 wt %, preferably in the range of 0.1 to 5.0 wt %, more preferably in the range of 0.1 to 1.0 wt %, even more preferably in the range of 0.3 to 1.0 wt % of the total weight of the sample diluent.

The vinyl-based water-soluble polymer used for the diluent used in the present invention is preferably a vinyl-based water-soluble polymer having a polar group containing an oxygen atom and a nitrogen atom, and examples thereof include polymers having a structural unit obtained by cleaving the double bond of a vinyl-based monomer such as acrylamide, methacrylamide, dimethylacrylamide, dimethylmethacrylamide, or vinylpyrrolidone. The vinyl-based water-soluble polymer used in the present invention may be one copolymerized with, for example, 50 mol % or less, preferably 30 mol % or less, particularly preferably 15 mol % or less of a vinyl-based monomer having an oxygen atom-containing polar group, such as vinyl alcohol, vinyl acetate, or an alkyl acrylate. Preferred specific examples of the vinyl-based water-soluble polymer used in the present invention include non-ionic polymers such as polyvinylpyrrolidone, dimethylacrylamide/vinylpyrrolidone copolymers (whose copolymerization ratio of dimethylacrylamide is 50 mol % or less), vinyl alcohol/vinylpyrrolidone copolymers (whose copolymerization ratio of vinyl alcohol is 50 mol % or less), and vinyl acetate/vinylpyrrolidone copolymers (whose copolymerization ratio of vinyl acetate is 20 mol % or less). These vinyl-based water-soluble polymers have a molecular weight of 10000 to 1000000, preferably 100000 to 1000000, more preferably 200000 to 500000. The vinyl-based water-soluble polymer content of the sample diluent is not particularly limited, but is in the range of 0.01 to 5.0 wt %, preferably in the range of 0.1 to 2.0 wt % of the total weight of the sample diluent.

The sample diluent is preferably an aqueous solution containing 0.1 to 1 wt % of a non-ionic surfactant, 0.05 to 0.2 M of an alkali metal inorganic salt, a buffering agent with a pH of 7 to 11, and 0.1 to 1 wt % of a vinyl-based water-soluble polymer. More preferably, the sample diluent is an aqueous solution containing 0.1 to 1 wt % of a non-ionic surfactant with an HLB value of 13 to 18, 0.05 to 0.2 M of an alkali metal inorganic salt, a Tris buffering agent or Good's buffering agent with a pH of 7 to 11, and 0.1 to 1 wt % of a vinyl-based water-soluble polymer having a polar group containing a nitrogen atom and an oxygen atom.

In the present invention, the sample diluent can be used to dilute a solid-containing viscous sample such as nasal swab. The dilution of a sample with the sample diluent prevents the clogging of the chromatography medium with the sample and facilitates the movement of the sample. Further, non-specific adsorption of components dissolved in the sample to the chromatography medium can also be prevented.

In the present invention, the sample diluent can also be used as a developer for developing a sample having a small liquid volume. When the liquid volume of a sample is small and therefore the sample supplied to the sample addition part does not reach the absorption part, the sample diluent used in the present invention is additionally supplied to allow the sample to pass through the determination region and reach the absorption part with reliability.

The sample diluent is included in a test kit according to the present invention together with the immunochromatography device.

The RSV test kit according to the present invention includes at least the immunochromatography device and the sample diluent, and optionally includes the labeling reagent solution.

If necessary, the test kit according to the present invention may further include a sample collection tool, a sample filter, a positive control, and a negative control. The sample collection tool may be appropriately selected depending on the properties of a sample, for example, a sterile cotton swab. The sample filter is used for, for example, filtering out solids from a collected sample itself or a sample diluted with the sample diluent.

Hereinbelow, the principles of detecting RSV according to the present invention will be described.

When a sample liquid containing an RSV antigen is supplied to the sample addition part of the immunochromatography device, the sample liquid reaches the chromatograph medium by capillary action and moves in the chromatography medium.

The sample liquid is mixed with the labeling reagent solution before the sample liquid is supplied, or the labeling reagent held in the labeling reagent-holding part is dissolved in the sample liquid, or the labeling reagent solution is supplied after the sample liquid is supplied so that the RSV antigen contained in the sample liquid binds to the labeling reagent.

The RSV antigen passes through the determination region of the chromatography medium together with the labeling reagent. The RSV antigen is captured in the determination region by the immobilized anti-F protein antibody or anti-N protein antibody through contact between the sample liquid and the antibody.

The excess sample and labeling reagent further move in the chromatography medium and are then absorbed by the absorption part.

When a sample contains an RSV antigen, an F protein antigen and/or an N protein antigen binding to the labeling reagent are/is captured in the determination region so that a visible signal appears in the determination region. That is, a clear signal appearing in the determination region means that the sample contains RSV, and the sample is determined as positive.

On the other hand, when a sufficient amount of RSV antigen binding to the labeling reagent is not captured in the determination region, no signal appears in the determination region. This generally means that a sample does not contain RSV or the amount of RSV contained in a sample is below the detection limit. In this case, the sample is determined as negative.

The specific procedure of an RSV detection method according to the present invention will be exemplified below.

(1) A sample liquid is supplied to an immunochromatography device in which at least one antibody that specifically binds to the F protein of RSV and at least one antibody that specifically binds to the N protein of RSV are immobilized on a determination region.

(2) A labeling reagent solution is supplied to the immunochromatography device concurrently with or subsequently to the supply of the sample liquid.

(3) A sample is allowed to pass through the determination region together with a labeling reagent to bring the sample into contact with the antibody immobilized on the determination region.

(4) The determination region is observed to detect coloring caused by the labeling reagent.

(5) When the coloring is detected, the sample is determined as "RSV positive", and when the coloring is not detected, the sample is determined as "RSV negative".

It is to be noted that the sample liquid in the process (1) may be prepared by diluting a sample with a sample diluent. Further, the process (2) is optional and may be omitted when, for example, the immunochromatography device includes a labeling reagent-holding part.

The detection of RSV contained in a sample can be performed according to the above procedure. Particularly, when the detection of RSV is performed according to the above procedure, a virus detection rate can be significantly increased as compared to when a conventional immunochromatographic test method is used.

Hereinbelow, the present invention will be more specifically described with reference to examples, but is not limited to these examples.

EXAMPLES

Example 1

(1) Preparation of Anti-RSV Monoclonal Antibody

BALB/c mice were immunized with a purified RSV strain or RSV-infected cells. In order to determine whether the titer of antibody against the F protein or N protein of RSV was increased, blood samples were collected from the mice. The spleen was harvested from each of the mice having increased antibody titers, and spleen cells were fused with mouse myeloma cells by a method proposed by Kohler et al. (Kohler et al., Nature, vol, 256, p 495 to 497 (1975)).

The thus obtained fused cells (hybridomas) were cultured in an incubator at 37° C., and the antibody titers in culture supernatants were determined by ELISA using plates on which the F protein antigen or N protein antigen of RSV was immobilized. The hybridomas whose culture supernatants had increased titers of antibody against an F protein or N protein derived from each of the subtypes A and B of RSV were selected. Further, the hybridomas were purified (singly cloned) by cloning.

The singly-cloned antibody-producing hybridomas were injected into the peritoneal cavity of pristane-treated BALB/c mice, and after about 2 weeks, antibody-containing ascites was collected. IgG was purified from the obtained ascites by affinity purification using Protein A column chromatography (manufactured by Amersham) to obtain an anti-F protein monoclonal antibody or an anti-N protein monoclonal antibody.

(2) Preparation of Determination Region of Chromatography Medium

The anti-F protein monoclonal antibody and the anti-N protein monoclonal antibody prepared in the above (1) were mixed in a weight ratio of 1:1 and diluted with a phosphate buffer solution (pH 7.4) containing 5 wt % of isopropyl alcohol to prepare an antibody solution having a concentration of 0.5 mg/mL.

A 25×2.5 cm nitrocellulose membrane (manufactured by Millipore, HF120) was coated with the antibody solution using an antibody coater (manufactured by BioDot), dried at 50° C. for 30 minutes, and then dried overnight at room temperature to prepare a determination region in the chromatography medium.

(3) Preparation of Labeling Reagent Solution

A labeling reagent was prepared using an anti-F protein antibody or an anti-N protein antibody obtained from a clone different from the clone which produced the anti-F protein antibody or the anti-N protein antibody used for the determination region.

The anti-F protein monoclonal antibody or the anti-N protein monoclonal antibody of 0.1 mL diluted with a HEPES buffer solution (pH 7.5) to a concentration of 0.1 mg/mL was added to 0.5 mL of a gold colloidal suspension (manufactured by Tanaka Kikinzoku Kogyo, average particle diameter: 40 nm), and the resulting mixture was allowed to stand at room temperature for 10 minutes. Then, 0.1 mL of a HEPES buffer solution (pH 7.5) containing 10 wt % of bovine serum albumin was added thereto, and the resulting mixture was allowed to stand at room temperature for 10 minutes. Then, the mixture was sufficiently stirred and then centrifuged at 8000×g for 15 minutes to remove a supernatant. Then, 0.1 mL of a phosphate buffer solution (pH 7.4) containing 1 wt % of bovine serum albumin was added to prepare an anti-F protein antibody-containing labeling reagent solution or an anti-N protein antibody-containing labeling reagent solution.

(4) Preparation of Immunochromatography Device

The thus prepared anti-F protein antibody-containing labeling reagent solution and anti-N protein antibody-containing labeling reagent solution were mixed in a volume ratio of 1:1. The resulting labeling reagent solution mixture of 200 μL was mixed with 100 μL of a 25 wt % aqueous trehalose solution, and the resulting mixture was evenly added to a 16 mm×100 mm glass fiber pad (manufactured by Millipore) and dried in a vacuum drier to prepare a labeling reagent-holding part.

Then, the chromatography medium having a determination region, the labeling reagent-holding part, and a glass fiber sample pad serving as a sample addition part, and an absorption pad for absorbing an excess sample or labeling substance were attached to a plastic backing sheet. Then, the thus obtained product was cut with a cutter to have a width of 5 mm to produce an immunochromatography device.

(5) Preparation of Sample Diluent

A solution was prepared using 0.5% Tween 20, 0.6% polyvinyl pyrrolidone (PVP) K-90 (molecular weight 360000), and a Tris buffer solution (pH 8.0) containing 1.0% bovine serum albumin and 150 mM sodium chloride. The solution was used as a sample diluent for diluting a sample such as nasal swab, pharyngeal swab, nasal aspirate, nasal discharge, or nasal wash.

(6) Measurement

The presence or absence of RS virus in a sample was determined in the following manner using the immunochromatography device and the sample diluent prepared above.

Nasal discharge samples were collected from RSV-infected people and diluted 10-fold, 50-fold, and 100-fold with the sample diluent. Each of the thus prepared samples of 120 μL was supplied onto the sample pad of the immunochromatography device and was developed. After 10 minutes, the determination region was visually observed to make a judgement according to the following criteria:

+++: A red line could be clearly observed in the determination region;
++: A red line could be observed in the determination region;
+: A red line could be observed but its color was light; and
−: A red line could not be observed.

The results are shown in Table 1.

Comparative Example 1

(1) Preparation of Determination Region of Chromatography Medium

A determination region was prepared in a chromatography medium in the same manner as in the above (2) of Example 1 except that only an anti-F protein monoclonal antibody was used. The anti-F protein monoclonal antibody used was derived from the same clone as the antibody used in the determination region in Example 1.

(2) Preparation of Immunochromatography Device

A labeling reagent solution containing only an anti-F protein antibody was prepared in the same manner as in the above (3) of Example 1, and an immunochromatography device was prepared in the same manner as in the above (4) of Example 1.

(3) Measurement

Samples were measured in the same manner as in the above (6) of Example 1 using the sample diluent described in the above (5) of Example 1. The results are shown in Table 1.

Comparative Example 2

(1) Preparation of Determination Region of Chromatography Medium

A determination region was prepared in a chromatography medium in the same manner as in the above (2) of Example 1 except that only an anti-F protein monoclonal antibody was used. The anti-F protein monoclonal antibody used was derived from a clone different from the clone which produced the antibody used for the determination region in Example 1.

(2) Preparation of Immunochromatography Device

A labeling reagent solution containing only an anti-F protein antibody was prepared in the same manner as in the above (3) of Example 1, and an immunochromatography device was prepared in the same manner as in the above (4) of Example 1.

(3) Measurement

Samples were measured in the same manner as in the above (6) of Example 1 using the sample diluent described in the above (5) of Example 1. The results are shown in Table 1.

Comparative Example 3

(1) Preparation of Determination Region of Chromatography Medium

A determination region was prepared in a chromatography medium in the same manner as in the above (2) of Example 1 except that only an anti-N protein monoclonal antibody was used. The anti-N protein monoclonal antibody used was derived from the same clone as the antibody used in the determination region in Example 1.

(2) Preparation of Immunochromatography Device

A labeling reagent solution containing only an anti-N protein antibody was prepared in the same manner as in the above (3) of Example 1, and an immunochromatography device was prepared in the same manner as in the above (4) of Example 1.

(3) Measurement

Samples were measured in the same manner as in the above (6) of Example 1 using the sample diluent described in the above (5) of Example 1. The results are shown in Table 1.

Comparative Example 4

(1) Preparation of Determination Region of Chromatography Medium

A determination region was prepared in a chromatography medium in the same manner as in the above (2) of Example 1 except that only an anti-N protein monoclonal antibody was used. The anti-N protein monoclonal antibody used was derived from a clone different from the clone which produced the antibody used for the determination region in Example 1.

(2) Preparation of Immunochromatography Device

A labeling reagent solution containing only an anti-N protein antibody was prepared in the same manner as in the above (3) of Example 1, and an immunochromatography device was prepared in the same manner as in the above (4) of Example 1.

(3) Measurement

Samples were measured in the same manner as in the above (6) of Example 1 using the sample diluent described in the above (5) of Example 1. The results are shown in Table 1.

TABLE 1

| Sample No. | Sample Dilution Rate | Example 1 | Comparative Example 1 | Comparative Example 2 | Comparative Example 3 | Comparative Example 4 |
|---|---|---|---|---|---|---|
| 1 | ×10 | +++ | + | − | +++ | +++ |
|   | ×50 | + | − | N.D. | ++ | N.D. |
|   | ×100 | + | − | N.D. | ++ | N.D. |
| 2 | ×10 | +++ | +++ | +++ | ++ | + |
|   | ×50 | ++ | ++ | N.D. | + | N.D. |
|   | ×100 | + | + | N.D. | − | N.D. |

Example 2

Study of Antibody Ratio in Determination Region (1) Preparation of Determination Region of Chromatography Medium A determination region was prepared using the same anti-F protein monoclonal antibody and anti-N protein monoclonal antibody as used in the above (2) in Example 1. More specifically, a determination region was prepared in the same manner as in the above (2) in Example 1 except that the mixing ratio between the anti-F protein antibody (anti-FP antibody) and the anti-N protein antibody (anti-NP antibody) was changed to 2:1, 1:1, 1:2, 1:3, 1:4, and 1:5.

(2) Preparation of Immunochromatography Device

An anti-F protein antibody-containing labeling reagent and an anti-N protein antibody-containing labeling reagent were prepared in the same manner as in the above (3) in Example 1. These reagents were mixed in different mixing ratios of 2:1, 1:1, 1:2, 1:3, 1:4, and 1:5 to obtain mixed solutions, and an immunochromatography device was produced in the same manner as in the above (4) in Example 1 using each of the mixed solutions.

(3) Measurement

Samples were measured in the same manner as in the above (6) in Example 1 using the sample diluent described in the above (5) in Example 1. The results are shown in Table 2.

Measurement of Sample 1 (Sample Dilution 50-Fold)

TABLE 2

| Antibody Ratio in Determination Region Anti-FP Antibody/Anti-NP Antibody | Antibody Ratio in Labeling Reagent Anti-FP Antibody/Anti-NP Antibody | | | | | |
|---|---|---|---|---|---|---|
| | 2/1 | 1/1 | 1/2 | 1/3 | 1/4 | 1/5 |
| 2/1 | + | + | + | + | + | + |
| 1/1 | ++ | + | ++ | ++ | ++ | ++ |
| 1/2 | + | + | ++ | ++ | ++ | ++ |
| 1/3 | + | ++ | ++ | ++ | ++ | ++ |
| 1/4 | ++ | + | ++ | ++ | ++ | ++ |
| 1/5 | + | + | ++ | ++ | ++ | ++ |

Measurement of Sample 2 (Sample Dilution 50-Fold)

TABLE 3

| Antibody Ratio in Determination Region Anti-FP Antibody/Anti-NP Antibody | Antibody Ratio in Labeling Reagent Anti-FP Antibody/Anti-NP Antibody | | | | | |
|---|---|---|---|---|---|---|
| | 2/1 | 1/1 | 1/2 | 1/3 | 1/4 | 1/5 |
| 2/1 | + | + | + | + | + | + |
| 1/1 | ++ | ++ | + | + | + | + |
| 1/2 | ++ | ++ | + | + | + | + |
| 1/3 | ++ | ++ | ++ | ++ | ++ | ++ |
| 1/4 | ++ | ++ | ++ | ++ | ++ | ++ |
| 1/5 | ++ | ++ | ++ | ++ | + | + |

According to the results of Comparative Examples 3 and 4 shown in Table 1, an RSV antigen is present in both Samples 1 and 2. However, an F protein antigen contained in Sample 2 is easily captured by the anti-F protein antibody, whereas an F protein antigen contained in Sample 1 is difficult to be captured by the anti-F protein antibody. The F protein contained in a sample varies in its ease of being captured on the determination region. The results shown in Tables 2 and 3 indicate that a stronger positive signal can always be obtained when the anti-F protein antibody is immobilized on the determination region in combination with the anti-N protein antibody which is more than the anti-F protein antibody in mixing ratio. That is, immobilization of a larger amount of the anti-N protein antibody on the determination region makes it possible to provide an immunochromatography device capable of achieving sensitive detection irrespective of the properties of an RSV antigen contained in a sample.

INDUSTRIAL APPLICABILITY

According to the present invention, an antibody that specifically binds to the F protein is used in combination with an antibody that specifically binds to the N protein in a determination region, which makes it possible to provide a high-sensitive immunochromatography device capable of significantly increasing an RSV detection rate as compared to a conventional immunochromatographic test kit.

Therefore, the present invention is useful in the industrial field of clinical tests for RSV infections, and therefore has industrial applicability.

The invention claimed is:

1. An immunochromatography device comprising a chromatography medium having a determination region on which at least one antibody that specifically binds to an F protein of RSV and at least one antibody that specifically binds to an N protein of RSV are jointly immobilized.

2. The immunochromatography device according to claim 1, comprising a sample addition part, the chromatography medium, and an absorption part.

3. The immunochromatography device according to claim 2, further comprising a labeling reagent-holding part.

4. The immunochromatography device according to claim 1, wherein the antibody that specifically binds to the F protein is at least one antibody that specifically binds to one or both of an F protein of subgroup A of RSV and an F protein of subgroup B of RSV.

5. An immunochromatographic test kit for RSV comprising: an immunochromatography device comprising a chromatography medium having a determination region on which at least one antibody that specifically binds to an F protein of RSV and at least one antibody that specifically binds to an N protein of RSV are jointly immobilized; and a sample diluent.

6. The immunochromatographic test kit for RSV according to claim 5, wherein the immunochromatography device includes a sample addition part, the chromatography medium, and an absorption part.

7. The immunochromatographic test kit for RSV according to claim 6, wherein the immunochromatography device further includes a labeling reagent-holding part.

8. The immunochromatographic test kit for RSV according to claim 6, further comprising a labeling reagent solution.

9. The immunochromatography device according to claim 2, wherein the antibody that specifically binds to the F protein is at least one antibody that specifically binds to one or both of an F protein of subgroup A of RSV and an F protein of subgroup B of RSV.

10. The immunochromatography device according to claim 3, wherein the antibody that specifically binds to the F protein is at least one antibody that specifically binds to one or both of an F protein of subgroup A of RSV and an F protein of subgroup B of RSV.

* * * * *